United States Patent [19]

Austin

[11] Patent Number: 5,290,810

[45] Date of Patent: Mar. 1, 1994

[54] COMPOUND, USE AND PREPARATION

[75] Inventor: Peter W. Austin, Bury, England

[73] Assignee: Imperial Chemical Industries PLC, London, England

[21] Appl. No.: 764,643

[22] Filed: Sep. 24, 1991

[30] Foreign Application Priority Data

Sep. 26, 1990 [GB] United Kingdom ............... 9020924

[51] Int. Cl.$^5$ .................................... C07C 331/08
[52] U.S. Cl. ............................ 514/516; 560/308; 560/309; 564/189; 564/191; 558/10; 514/517
[58] Field of Search ............. 558/10; 564/189, 191; 560/308, 309; 514/516, 517

[56] References Cited

FOREIGN PATENT DOCUMENTS

| 0018100 | 3/1980 | European Pat. Off. ............ 548/213 |
| 0152591 | 12/1984 | European Pat. Off. ............ 564/189 |
| 0342105 | 5/1989 | European Pat. Off. ............ 564/189 |
| 3307733 | 3/1983 | Fed. Rep. of Germany ...... 548/213 |
| 2087388 | 10/1981 | United Kingdom ................ 548/213 |
| 2176187 | 6/1986 | United Kingdom ................ 558/10 |

Primary Examiner—Mary C. Lee
Assistant Examiner—Joseph K. McKane
Attorney, Agent, or Firm—Cushman, Darby & Cushman

[57] ABSTRACT

A compound of the formula

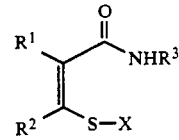

in which $R^1$ and $R^2$ taken together represent a polymethylene chain having 3 or 4 carbon atoms, or a polymethylene chain having 3 or 4 carbon atoms substituted by at least one lower alkyl radical having 1 to 4 carbon atoms, $R^3$ is hydrogen, hydrocarbyl or substituted hydrocarbyl and X represents cyano, a group —$SO_3M$ or a group —S—$R^4$ where M is hydrogen or an alkali metal such as sodium and $R^4$ is hydrocarbyl or substituted hydrocarbyl. Typically $R^1$ and $R^2$ complete a cyclopentene ring, $R^3$ is alkyl such as methyl and X is a group —$SO_3Na$. The compounds have microbiological activity.

23 Claims, No Drawings

COMPOUND, USE AND PREPARATION

The present invention relates to compounds which are useful as industrial biocides and to the use and preparation of such compounds.

Industrial biocides are useful to prevent industrial spoilage, in particular that caused by bacteria and fungi. Industrial biocides find application in the preservation of paints, latices, adhesives, leather, wood, metal working fluids and cooling water.

One class of compound which can be used as an industrial biocide is based on the isothiazolinone structure. There are many disclosures of isothiazolinone derivatives which are stated to have useful biocidal properties. Thus, British Patent Specification 2087388 discloses 4,5-polymethylene-4-isothiazolin-3-ones in which the polymethylene chain contains 3 or 4 carbon atoms.

Certain isothiazolin-3-one systems have also been ring-opened to form 2-aminocarbonylvinylthiosulphate derivatives as described in German Patent DE 3307733. Some of these compounds exhibit surprisingly effective biocidal properties.

However, as with all industrial biocides none are ideal. Some exhibit deficiencies in chemical stability, others suffer from inadequate control of certain microorganisms. Consequently, research continues to find better and more cost effective industrial biocides.

We have now found that certain ring-opened derivatives of the 4,5-polymethylene-4-isothiazolin-3-ones exhibit surprising chemical stability and are effective as industrial biocides, especially as industrial bactericides.

According to the present invention, there is provided a compound of the general formula I

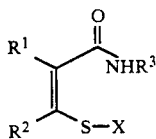
I wherein
$R^1$ and $R^2$ taken together represent a polymethylene chain having 3 or 4 carbon atoms or a polymethylene chain having 3 or 4 carbon atoms substituted by at least one lower alkyl radical having from 1 to 4 carbon atoms;
$R^3$ is hydrogen, hydrocarbyl or substituted hydrocarbyl; and
X represents cyano, a group —$SO_3M$ or a group —S—$R^4$,
M represents a cation having a valency and being in an amount to give a neutral compound; and
$R^4$ represents hydrocarbyl or substituted hydrocarbyl.

When $R^1$ and $R^2$ form a polymethylene chain substituted by lower alkyl, there may be present up to eight lower alkyl radicals. It is preferred, however, that $R^1$ and $R^2$ contain no alkyl substituents.

In one particular embodiment of the invention where $R^1$ and $R^2$ taken together form a polymethylene chain, the compound is one of general formula II

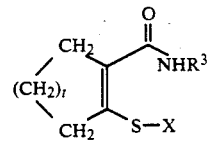
II wherein
$R^3$ and X are as defined; and
t is 1 or 2.
Preferably t is 1.

Where $R^3$ and $R^4$ are hydrocarbyl or substituted hydrocarbyl, each of $R^3$ and $R^4$ may contain up to 20 carbon atoms, and especially up to 12 carbon atoms.

When $R^3$ and $R^4$ are substituted hydrocarbyl, they are hydrocarbyl moieties containing up to 20 carbon atoms, and especially up to 12 carbon atoms which additionally contain at least one hetero atom selected from oxygen, nitrogen, sulphur and/or at least one halogen, for example, fluorine, chlorine and bromine.

It is generally preferred that $R^3$ is hydrogen or hydrocarbyl, especially $C_1$–$C_{12}$ alkyl, which may be linear or branched.

$R^4$ is preferably phenyl, benzyl and alkyl groups such as methyl, butyl, hexyl and octyl.

M is preferably hydrogen, an alkali metal or a quaternary ammonium ion and especially an alkali metal such as lithium, potassium or, more especially, sodium.

Particularly useful compounds are those of general formula I where X is cyano or a group —$SO_3M$ where M is as defined hereinbefore.

It will be appreciated that in many instances water solubility may be improved by using mixtures of compounds of general formula I, wherein X is a group $SO_3M$ with different values of M from those hereinbefore defined, especially different alkali metals.

A specific example of a compounds of general formula I where X is cyano is 2-methylaminocarbonyl-1-thiocyanatocyclopent-1-ene.

Specific examples of compounds of general formula I where X is a group —$SO_3M$, are
the sodium salt of 2-methylaminocarbonyl-1-thiosulphatocyclopent-1-ene,
the sodium salt of 2-butylaminocarbonyl-1-thiosulphatocyclopent-1-ene,
the sodium salt of 2-hexylaminocarbonyl-1-thiosulphatocyclopent-1-ene, and
the sodium salt of 2-octylaminocarbonyl-1-thiosulphatocyclopent-1-ene.

A specific example of a compound of general formula I where X is a group —S—$R^4$, is 1-tertiarybutyldithio-2-methylaminocarbonylcyclopentene.

The compounds of general formula I may be readily prepared by ring opening the isothiazolin-3-ones of general formula III

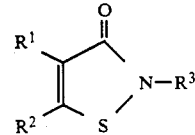
III by contacting with bisulphites, or with hydrosulphites or with thiols of general formula $R^4$-SH where $R^1$ to $R^4$ are all as previously defined.

The thiocyanates of general formula I where X is cyano are most conveniently prepared by reacting the thiosulphates of general formula I where X is a group $SO_3M$ with a source of cyanide ion.

The compounds of general formula I wherein X is the group $-SO_3M$ are readily prepared by reacting the isothiazolin-3-ones of general formula III with hydrosulphite ion, or bisulphite ion in a suitable solvent at temperatures which are not above 60° C., and especially at temperatures below 30° C. for example 0° to 20° C.

The solvent is generally selected to dissolve the isothiazolin-3-one of general formula III. Where $R^3$ contains relatively few carbon atoms, the isothiazolin-3-one may be sufficiently soluble in water for the reaction to be carried out under solely aqueous conditions. In other cases, it may be more appropriate to use a more polar solvent, such as an alkanol. Typically, the alkanol may be methanol or ethanol.

It will be readily appreciated that mixtures of such solvents can be used, including mixtures with water.

The reaction between the isothiazolin-3-one of general formula III and a bisulphite, hydrosulphite or thiol of formula $R^4SH$ can be readily carried out to give high yields of the compounds of general formula I simply by stirring together the isothiazolin-3-one with up to 10 moles of the bisulphite, hydrosulphite or thiol. Generally, at least one mole of the bisulphite, hydrosulphite or thiol is used per mole of isothiazolin-3-one, and typically between 1 and 3 moles of bisulphite, hydrosulphite or thiol per mole of isothiazolin-3-one.

Similarly, the thiocyanato compounds of general formula I where X is cyano can be readily prepared from the thiosulphates of general formula I where X is the group $SO_3M$ simply by stirring in solution with a source of cyanide ion, such as sodium or potassium cyanide. A molar excess of cyanide ion may be used, but for environmental reasons it is preferred to use stoichiometric proportions of cyanide ion and the thiosulphate compound.

The above reactions may be readily monitored in conventional manner, typically by sampling and analysing by High Performance Liquid Chromatography (HPLC).

The compounds of general formula I can, in some cases, be readily separated from the reaction mix by filtration. In many instances, they remain soluble in the solvent used and can be recovered simply by evaporating the solvent. However, on a laboratory scale, these compounds may be isolated in pure form by "flash chromatography". In such cases, the reaction mass is first dissolved completely by adding a polar solvent, if necessary, and is then deposited on a suitable support such as silica. The compounds of general formula I are then sequentially eluted under a solvent gradient of increasing polarity. The product may then be recovered in high yield, and of high degree of purity, simply by evaporating the solvent.

For some applications, it is convenient to formulate the compound of general formula I in solution, especially using water or polar organic solvents such as alcohols.

The compounds of general formula I have been found to have activity against a range of micro-organisms including bacteria, fungi and yeast, and are suitable for use as industrial biocides. They exhibit good wet state preservation and hence may be used as cutting fluid preservatives and also in cooling water applications. They may also be used in paper mill liquors. Furthermore, the compounds may be used to preserve industrially important formulations, especially aqueous based formulations, which are used for coloration, such as dyestuffs and printing inks. They may also be used in the agrochemical industries to preserve formulations such as herbicide and pesticide flowables.

Still further important applications of the compounds of the present invention include their use in hydrocarbon fluids such as diesel fuels. They may also be incorporated into adhesives and cosmetics in order to inhibit microbial spoilage.

The preservation of wood and leather is yet another important application of the compounds.

Especially important is the use of the compounds of the present invention in paints, particularly in aqueous based latices.

A particularly preferred use of the compounds of the present invention is the preservation of polyvinyl acrylate and particularly acrylic latices, especially those whose pH is above 7, and especially those containing ammonia or amines.

The compounds of the present invention may be used alone as an antimicrobial material but may also be used in, or on, a suitable carrier material.

Thus, as a further aspect of the present invention there is provided a biocide composition comprising a carrier and an effective amount of a compound of general formula I in accordance with the invention.

The carrier is typically a medium which shows little, if any, antimicrobial activity and may be, or include, a material which is susceptible to the growth of microorganisms, such as bacteria. The carrier is preferably a liquid medium and the biocide composition is preferably a solution, suspension or emulsion of the compound of general formula I in a liquid carrier. The carrier may be water, or a hydrophilic solvent such as acetic acid, N,N-dimethylformamide, propylene glycol, ethylene diomine, dimethyl sulphoxide or N-methyl-2-pyrrolidone or a mixture of such liquids. If the composition is in the form of a suspension or emulsion this preferably contains a surface active agent in order to inhibit phase preparation. Any surface active agent known for use in biocide compositions may be used in such a system, for example alkylene oxide adducts of fatty alcohols, alkyl phenols, amines such as ethylene diamine, and anionic surfactants such as those obtained by reacting naphthol sulphonates with formaldehyde.

The amount of the compound or compounds of general formula I which is present in the biocide composition may be just sufficient to have an antimicrobial effect or may be present substantially in excess of this amount. It will be appreciated that the biocide composition may be provided as a concentrated solution for bulk transportation and subsequently diluted for use in antimicrobial protection. Thus, the amount of the compound of general formula I which is present in the biocide composition is typically in the range from 0.0001% up to 30% by weight of the biocide composition.

The compositions can be used for the treatment of various media to inhibit the growth of micro-organisms. The composition of the present invention is especially effective in providing anti-bacterial activity.

As a further aspect of the present invention there is provided a method for inhibiting the growth of microorganisms on, or in, a medium which comprises treating the medium with a compound of the general formula I or a composition containing a compound of general formula I as hereinbefore defined.

The compound can be used in systems in which micro-organisms grow and cause problems. These systems include liquid, particularly aqueous, systems for example cooling water liquors, paper mill liquors, metal working fluids, geological drilling lubricants, polymer emulsions and surface coating compositions such as paints, varnishes and lacquers, and solid systems such as wood and leather. The compound of the present invention can be included in such systems to provide an antimicrobial effect. The amount of the compound is typically from 0.0001 up to 10%, preferably 0.001 up to 5% and especially 0.002 to 0.1% by weight relative to the system to which it is added. In many cases, microbial inhibition has been achieved with from 0.0005% to 0.01% by weight of the compound.

The compounds of general formula I may be the only biologically active compounds of the composition of the present invention or the composition may comprise further compounds having antimicrobial characteristics. The composition may contain more than one compound of general formula I. Alternatively, a composition of a compound of general formula I in accordance with the present invention may be used together with one or more other antimicrobial compounds. The use of a mixture of anti-microbial compounds can provide a composition having a broader anti-microbial spectrum and hence one which is more generally effective than the individual components thereof. The other antimicrobial may be one possessing anti-bacterial, anti-fungal, anti-algal or other antimicrobial characteristic. The mixture of the compound of the present invention with other antimicrobial compounds typically contains from 1 to 99% by weight, and particularly from 40 to 60% by weight, relative to the weight of total antimicrobially active compounds, of the composition of a compound of general formula I.

Examples of known antimicrobial compounds which may be used, together with the compound of general formula I are quaternary ammonium compounds such as diethyldodecylbenzyl ammonium chloride; dimethyloctadecyl(dimethylbenzyl)ammonium chloride; dimethyldidecylammonium chloride; dimethyldidodecylammonium chloride; trimethyl-tetradecylammonium chloride; benzyldimethyl($C_{12}$-$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecylbenzyltrimethylammonium chloride; benzyldimethyl($C_{12}$-$C_{18}$ alkyl) ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethylhexyl)-5-methyl-5-aminohexahydropyrimidine; hexamethylene tetra amine; 1,3-bis(4-aminophenoxy)propane; and 2-[(hydroxymethyl)amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2-bromo-2-bromomethylglutaronitrile, 2-chloro-2-chloromethylglutaronitrile, 2,4,5,6-tetrachloroisophthalodinitrile; thiocyanate derivatives such as methylene bisthiocyanate; tin compounds or complexes such as tributyltin-oxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methyl-isothiazolin-3-one, benzisothiazolin-3-one and 2-methylbenzisothiazolin-3-one; thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as gluteraldehyde (pentanedial), p-chlorophenyl-3-iodopropargyl formaldehyde and glyoxal; amides such as chloracetamide; N,N-bis(hydroxymethyl)chloracetamide; N-hydroxymethylchloracetamide and dithio-2,2-bis(benzmethyl amide); guanidine derivatives such as polyhexamethylene biguanide and 1,6-hexamethylene-bis[5-(4-chlorophenyl)-biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichloro-phenoxy)-phenol; thio-bis(4-chlorophenol) and 2-phenylphenol; sulphone derivatives such as diiodomethyl-paratolyl sulphone, 2,3,5,6-tetrachloro-4-(methylsulphonyl)pyridine and hexachlorodimethyl sulphone.

Further aspects of the present invention are described in the following illustrative examples.

In the following examples, all preparative details are given in parts by weight unless otherwise stated, and the compounds in accordance with the present invention were subjected to evaluation of the antimicrobial properties under sterile conditions as detailed below:

In the microbiological testing, the compounds were tested for anti-microbial activity against bacteria, fungi and a yeast. The bacteria used were one or more of *Escherichia coli, Pseudomonas aeruginosa, Staphylococcus aureus* and *Bacillus subtilis*. The fungi/yeast used were one or more of *Aspergillus niger, Candida albicans, Aureobasidium pullulans, Gliocladium roseum,* and *Penicillium pinophilum*.

These test organisms will be referred to hereafter as EC, PA, SA, BS, AN, CA, AP, GR and PP respectively.

Microbiological evaluation

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with bacteria, fungi and yeast. The plates were incubated for four days at 25° C.

At the end of the incubation period, the plates were assessed visually for growth of the micro-organisms. The concentration of the product which inhibited the growth of a particular micro-organism was recorded. This is the minimum inhibitory concentration (M.I.C.).

Generally, the compounds are evaluated against bacteria at the 25 and 100 ppm levels, and against fungi and yeast at the 5, 25 and 100 ppm levels.

EXAMPLE 1

Preparation of the sodium salt of 2-butylaminocarbonyl-1-thiosulphatocyclopent-1-ene.

2-butyl-4,5-trimethylene-4-isothiazolin-3-one (0.64 parts) were dissolved in distilled water (20 parts) with stirring and two portions of sodium hydrosulphite (2×0.2 parts) were added at 20°–25° C., and 30 minutes apart.

An immediate white precipitate formed, later becoming tarry. The reaction products were stirred overnight, and then dissolved by adding methanol (20 parts) and evaporated onto a silica support.

The reaction products were then separated by "flash chromatorgraphy". The silica support in the form of a column was eluted first with petroleum ether (boiling between 40° and 60° C.) followed by a mixture of petroleum ether containing increasing amounts of methylene chloride, where the methylene chloride was added in 10% increments by volume up to 100% methylene chloride. The column was the eluted with a mixture of methylene chloride and methanol, where the methanol was added in 1% increments by volume.

Each step change in the eluant system was carried out after 100 parts by volume of eluant.

The thiosulphate was eluted in fractions containing between 9 and 13% by volume methanol in methylene chloride. The various fractions were combined and the solvent evaporated to give the thiosulphate as a whitish solid (0.47 parts) softening at 120° C.

Proton NMR in deuterated dimethylsulphoxide gave the following results:

Proton NMR δ (DMSO): 0.85(3H, —CH$_3$); 1.25(2H, —CH$_2$—CH$_3$); 1.40(2H, —CH$_2$—CH$_2$—CH$_2$—); 1.85(2H, ring —CH$_2$—CH$_2$—CH$_2$—); 2.55(4H, (ring —CH$_2$—CH$_2$—C=)$_2$); 2.95(2H, —N—CH$_2$—); 7.60(1H, —NH—)

Carbon $^{13}$C NMR gave the following results:

$^{13}$C NMR δ (DMSO): 13.6(—C—CH$_3$); 19.5(—CH$_2$—CH$_3$); 21.6(—CH$_2$—CH$_2$—CH$_2$—); 30.9(—CH$_2$CH$_2$—CH$_2$—); 31.2(—N—CH$_2$—C—);

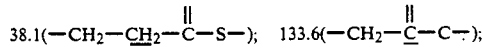

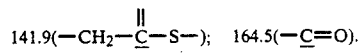

141.9(—CH$_2$—C—S—); 164.5(—C=O).

Microbiostatic evaluation of the thiosulphate gave the following MIC values

| EC | GT 100 ppm | AN | GT 100 ppm |
|----|-----------|----|-----------|
| PA | GT 100 ppm | CA | GT 100 ppm |
| SA | 25 ppm | AP | 25 ppm |
| BS | 25 ppm | GR | 25 ppm |
|    |           | PP | 100 ppm |

GT = Greater than.

EXAMPLE 2

Preparation of the sodium salt of 2-hexylaminocarbonyl-1-thiosulphatocyclopent-1-ene.

The procedure of Example 1 was repeated except 2-hexyl-4,5-trimethylene-4-isothiazolin-3-one (1.55 parts) was used in place of the 2-butyl-4,5-trimethylene-4-isothiazolin-3-one.

The reaction products were again separated by "flash chromatography" to give the sodium salt of 2-hexylaminocarbonyl-1-thiosulphatocyclopent-1-ene as a white solid (0.77 parts).

The thiosulphate gave the following NMR spectrum as a solution in deuterated dimethylsulphoxide Proton NMR δ (DMSO): 0.8(3H, CH$_3$—C); 1.2(8H, —CH$_2$—CH$_2$—CH$_2$—CH$_2$—CH$_3$); 1.4(2H, —N—CH$_2$—CH$_2$—C—); 1.9(2H, ring, —CH$_2$CH$_2$—CH$_2$—); 2.6(4H, ring —CH$_2$—CH$_2$—CH$_2$); 3.1(2H, —N—CH$_2$—C—); 7.6(1H, —NH—).

Microbiostatic evaluation gave the following results:

| EC | GT 100 ppm | AN | 25 ppm |
|----|-----------|----|--------|
| PA | GT 100 ppm | CA | 100 ppm |
| SA | 25 ppm | AP | 25 ppm |
| BS | 25 ppm | GR | 100 ppm |
|    |           | PP | 25 ppm |

GT = Greater than.

EXAMPLE 3

Preparation of the sodium salt of 2-octylaminocarbonyl-1-thiosulphate cyclopent-1-ene.

2-octyl-4,5-trimethylene-4-isothiazolin-3-one (1.0 parts) was stirred overnight at 20°–25° C. in distilled water (25 parts) and sodium hydrosulphite (0.2 parts). Analysis by high performance liquid chromatography (HPLC) showed the presence of about 33% starting material. A further portion of sodium hydrosulphite (0.2 parts) was added and the reactants stirred at 20°–25° C. for a further 1 hour. Analysis by HPLC showed the reaction to be still incomplete, hence a further aliquot of hydrosulphite (0.2 parts) was added and the reactants stirred for a further 2 hours. The reaction then appeared complete by HPLC.

A precipitate was formed and was filtered off, and washed with water.

The filtrate and washings from the above were evaporated onto silica and the hydrosulphite separated by "flash chromatography". The silica column was first eluted with methylene chloride and then a mixture of methylene chloride and methanol where the amount of methanol was increased in 1% increments by volume. The amount of methanol was increased stepwise in 100 parts by volume aliquots.

The thiosulphate was eluted in the methylene chloride fractions containing from 8 to 11% by volume methanol. These fractions were combined, and the solvent evaporated to give the thiosulphate as a white solid (0.62 parts), softening at 99° C.

Proton NMR in deuterated dimethylsulphoxide solution gave the following results:

Proton NMR δ (DMSO): 0.9(3H, CH$_3$—C—); 1.25(10H, —C—(CH$_2$)$_5$—C—); 1.45(2H, —N—CH$_2$—CH$_2$—); 1.9(2H, ring —CH$_2$—CH$_2$—CH$_2$—); 2.6(2H, ring

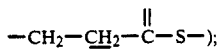

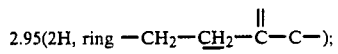

3.10(2H, —N—C$\underline{H}$$_2$—C—);

7.65(1H, —N$\underline{H}$—).

Microbiostatic evaluation gave the following MIC values:

| EC | 100 ppm | AN |  | GT 100 ppm |
|----|---------|----|----|------------|
| PA | GT 100 ppm | CA |  | GT 100 ppm |
| SA | 100 ppm | AP |  | 100 ppm |
| BS | 100 ppm | GR |  | 100 ppm |
|    |         | PP |  | 100 ppm |

GT = Greater than

EXAMPLE 4

Preparation of the sodium salt of 2-methylaminocarbonyl-1-thiosulphatocyclopent-1-ene.

2-methyl-4,5-trimethylene-4-isothiazolin-3-one (1 part) was stirred in distilled water (25 parts) at 20° to 25° C. Sodium hydrosulphite (2×0.2 parts) was added in two portions over 30 minutes. Analysis by HPLC indicated the formation of two products.

The white solid which formed was filtered off, and the filtrate was evaporated onto silica, and the product separated by "flash chromatography". The silica in the form of a column was eluted first with petroleum ether (boiling range 40°–60° C.) and then a mixture of petroleum ether and methylene chloride where the latter increased in 10% by volume increments and stepwise in 100 parts by volume intervals. The column was then eluted with a mixture of methylene chloride and methanol, where the latter increased in intervals of 2% by volume and again in stepwise aliquots of 100 parts by volume.

The thiosulphate was eluted in the methylene chloride fractions containing between 12 and 18% by volume methanol.

These fractions were combined, and the solvent evaporated to give a white solid (0.97 parts), and melting above 305° C.

Elemental analysis gave the following results:

| C$_7$H$_{10}$NO$_4$S$_2$Na.H$_2$O requires | 3.18% C | 4.6% H | 4.9% N | 21.5% S | 6.6% Na |
|---|---|---|---|---|---|
| | 30.3% C | 4.3% H | 5.1% N | 23.1% S | 8.3% Na |

Proton NMR analysis in deuterated water gave the following results:

Proton NMR δ(D$_2$O): 2.06(2H, CH$_2$—C$\underline{H}$$_2$—CH$_2$—);

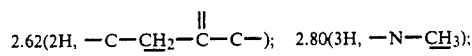

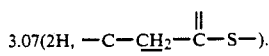

Microbiostatic evaluation gave the following results:

| EC | 25 ppm | AN | 100 ppm |
|----|--------|----|---------|
| PA | 100 ppm | CA | 25 ppm |
| SA | 25 ppm | AP | 100 ppm |
| BS | 25 ppm | GR | 25 ppm |
|    |        | PP | 25 ppm |

EXAMPLE 5

Preparation of 2-methylaminocarbonyl-1-thiocyanatocyclopent-1-ene.

The sodium salt of 2-methylaminocarbonyl-1-thiosulphatocyclopent-1-ene (1.14 parts) whose preparation is described in Example 4 was dissolved in distilled water (10 parts) and stirred for 2 hours at 20°–25° C. with potassium cyanide (0.26 parts). An immediate white precipitate was formed consisting of the thiocyanate which was filtered, washed with water and dried giving a white solid (0.55 parts) melting at 181°–183° C.

Elemental analysis gave the following results

| C$_8$H$_{10}$NO$_2$OS.0.5H$_2$O | 49.9% C | 5.4% H | 14.2% N | 16.6% S |
|---|---|---|---|---|
| requires | 50.3% C | 5.8% H | 14.7% N | 16.8% S |

Proton NMR in deuterated dimethylsulphoxide gave the following results:

Proton NMR: δ(DMSO): 2.0(2H, —CH$_2$—C$\underline{H}$$_2$—CH$_2$—);

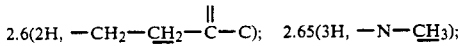

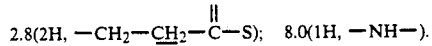

Carbon $^{13}$C NMR gave the following results:

$^{13}$C NMR δ(DMSO): 2.17(—CH$_2$—C$\underline{H}$$_2$—CH$_2$);

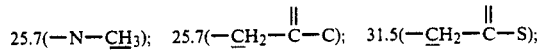

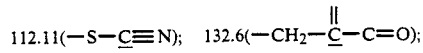

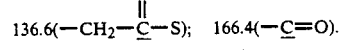

Microbiostatic evaluation gave the following MIC values

| EC | 25 ppm | AN | GT 100 ppm |
|----|--------|----|------------|
| PA | GT 100 ppm | CA | 25 ppm |
| SA | 25 ppm | AP | 25 ppm |
| BS | 25 ppm | GR | 25 ppm |

| | |
|---|---|
| | -continued |
| | PP NA |

NA = Not available

EXAMPLE 6

A mixed inoculum was prepared by culturing the following organisms for 24 hrs at 30° C. on nutrient agar.

| | |
|---|---|
| *Aeromonas hydrophila* | (P.R.A. 8) |
| *Proteus rettgeri* | (NCIB 10842) |
| *Pseudomonas aeruginosa* | (BSI ex P.R.A.) |
| *Serratia marcescens* | (NCIB 9523) |
| *Alcaligenes sp.* | (Lab. isolate AC4) |
| *Pseudomonas cepacea* | (Lab. isolate AC5) |
| *Pseudomonas putida* | (Lab. isolate AC7) |

Suspensions of each organism were prepared at a concentration of approximately $1 \times 10^8$ cells/ml (Thoma counting chamber) in quarter-strength by volume of Ringers solution. A mixed inoculum was prepared by combining equal volumes of each bacterial suspension.

The sodium salt of 2-methylaminocarbonyl-1-thiosulphatocyclopent-1-ene, prepared as described in Example 4, was incorporated in 50 gm aliquots of a standard acrylic emulsion paint containing 0.2% by weight of yeast extract at the concentrations by weight indicated in the following table. These samples were inoculated on 3 separate occasions, at weekly intervals, with 1 part by volume of the mixed inoculum, and incubated at 30° C.

After contact times of 1, 3 and 7 days, a small aliquot from each sample was streaked across the surface of a nutrient agar plate and incubated at 30° C. for 2 days. The presence or absence of bacterial growth was determined visually.

The results are displayed in table 1 below, including a control containing no thiosulphatocyclopent-1-ene as biocide.

TABLE 1

| | | Bacterial growth (a) | | | | | | | | |
|---|---|---|---|---|---|---|---|---|---|---|
| | Concn | Week 1 Time (days) | | | Week 2 Time (days) | | | Week 3 Time (days) | | |
| Sample | (ppm) | 1 | 3 | 7 | 1 | 3 | 7 | 1 | 3 | 7 |
| Example 4 | 100 | 0 | 0 | 0 | 0 | 0 | 0 | 0 | 0 | 0 |
| | 50 | 0 | 0 | 0 | 0 | 0 | 0 | 0 | 0 | 0 |
| | 25 | 2 | 0 | 0 | 1 | 1 | 0 | 1 | 0 | 0 |
| | 12.5 | 3 | 3 | 0 | 3 | 2 | 0 | 3 | 1 | 0 |
| | 5.0 | 3 | 3 | 0 | 3 | 2 | 0 | 3 | 1 | 0 |
| | 2.5 | 3 | 3 | 0 | 3 | 2 | 0 | 3 | 2 | 0 |
| Control | 0 | 4 | 4 | 4 | 4 | 4 | 4 | 4 | 4 | 4 |

Notes to Table 1
(a)
0 means no growth (no visible colonies)
1 means a trace of growth visible
2 means a light growth (a few colonies visible)
3 means moderate growth (discrete colonies visible, possibly with some coalescence)
4 means dense/confluent growth (coalescing colonies visible throughout).

EXAMPLE 7

Preparation of 1-tertiarybutyldithio-2-methylaminocarbonylcyclopentene.

2-methyl-4,5-trimethylene-4-isothiazolin-3-one (0.78 parts) and sodium tertiary butyl mercaptan (0.56 parts) were stirred together in methanol (10 parts by volume) at 20° to 25° C. for 1 hour. The reactants were then drowned out into distilled water (100 parts by volume) and the disulphide reaction product (1 part) which separated was filtered and dried. The disulphide melted at 153°−5° C.

Elemental analysis for the disulphide gave the following results:

| | | | | |
|---|---|---|---|---|
| $C_{11}H_{19}NOS_2$ requires | 53.8% C, | 8.0% H, | 5.3% N | 25.0% S |
| | 53.9% C, | 7.8% H, | 5.7% N | 26.1% S |

Microbiostatic evaluation of the disulphide gave the following MIC values.

| | | | |
|---|---|---|---|
| EC | 25 ppm | AN | GT 100 ppm |
| PA | GT 100 ppm | CA | GT 100 ppm |
| SA | GT 100 ppm | AP | GT 100 ppm |
| BS | 100 ppm | GR | GT 100 ppm |
| | | PP | GT 100 ppm |

I claim:

1. A compound of the general formula I

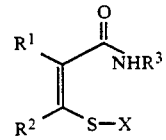

wherein
$R^1$ and $R^2$ taken together represent a polymethylene chain having 3 or 4 carbon atoms or a polymethylene chain having 3 or 4 carbon atoms substituted by at least one lower alkyl radical having from 1 to 4 carbon atoms;
$R^3$ is hydrogen, hydrocarbyl or hydrocarbyl substituted with at least one atom selected from the group consisting of oxygen, nitrogen, sulphur and halogen;
X represents cyano, a group —SO₃M or a group —S—R⁴;
M represents a cation having a valency and being in an amount to give a neutral compound; and
$R^4$ represents hydrocarbyl or hydrocarbyl substituted with at least one atom selected from the group consisting of oxygen, nitrogen, sulphur and halogen.

2. A compound as claimed in claim 1 which has the general formula II

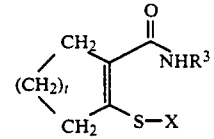

wherein
$R^3$ and X are as defined in claim 1; and
t is 1 or 2.

3. A compound as claimed in claim 2 wherein t is 1.

4. A compound as claimed in claim 1 wherein $R^3$ is hydrocarbyl or substituted hydrocarbyl containing up to 20 carbon atoms.

5. A compound as claimed in claim 4 wherein $R^3$ is hydrocarbyl or substituted hydrocarbyl containing up to 12 carbon atoms.

6. A compound as claimed in claim 5 wherein $R^3$ is alkyl.

7. A compound as claimed in claim 1 wherein $R^4$ is hydrocarbyl or substituted hydrocarbyl containing up to 20 carbon atoms.

8. A compound as claimed in claim 7 wherein $R^4$ is hydrocarbyl or substituted hydrocarbyl containing up to 12 carbon atoms.

9. A compound as claimed in claim 8 wherein $R^4$ is alkyl.

10. A compound as claimed in claim 1 wherein M is hydrogen, an alkali metal or a quaternary ammonium ion.

11. A compound as claimed in claim 10 wherein M is sodium.

12. A compound selected from
2-methylaminocarbonyl-1-thiocyanatocyclopent-1-ene,
the sodium salt of 2-methylaminocarbonyl-1-thiosulphatocyclopent-1-ene,
the sodium salt of 2-butylaminocarbonyl-1-thiosulphatocyclopent-1-ene,
the sodium salt of 2-hexylaminocarbonyl-1-thiosulphatocyclopent-1-ene,
the sodium salt of 2-octylaminocarbonyl-1-thiosulphatocyclopent-1-ene, or
1-tertiary butyldithio-2-methylaminocarbonylcyclopentene.

13. A medium which is susceptible to microbial attack having therein or thereon a compound as claimed in claim 1 in a sufficient amount to inhibit the growth of micro-organisms.

14. A medium which is susceptible to microbial attack which contains from 0.0001 to 30% by weight of the medium of a compound as claimed in claim 1.

15. A medium as claimed in claim 14 which contains from 0.002 to 0.1% by weight of the medium of the compound.

16. A medium as claimed in claim 15 which contains from 0.0005 to 0.01% by weight of the medium of the compound.

17. A medium as claimed in claim 13 which is selected from a cooling water system, a paper mill liquor, a metal working fluid, a geological drilling lubricant, a polymer emulsion, a latex, a paint, a lacquer, a varnish, a hydrocarbon fluid, an adhesive, a cosmetic, a dyestuff or ink formulation, an agrochemical formulation, leather or wood.

18. A paint medium as claimed in claim 17 which is an acrylic latex.

19. A composition comprising a carrier and a compound of general formula I

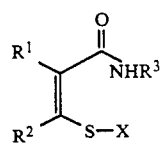

wherein
$R^1$ and $R^2$ taken together represent a polymethylene chain having 3 or 4 carbon atoms or a polymethylene chain having 3 or 4 carbon atoms substituted by at least one lower alkyl radical having from 1 to 4 carbon atoms;
$R^3$ is hydrogen, hydrocarbyl or hydrocarbyl substituted with at least one atom selected from the group consisting of oxygen, nitrogen, sulphur and halogen;
X represents cyano, a group $—SO_3M$ or a group $—S—R^4$;
M represents a cation having a valency and being in an amount to give a neutral compound; and
$R^4$ represents hydrocarbyl or hydrocarbyl substituted with at least one atom selected from the group consisting of oxygen, nitrogen, sulphur and halogen, 20. A method for inhibiting the growth of micro-organisms on, or in, a medium, which comprises treating the medium with a compound of general formula I

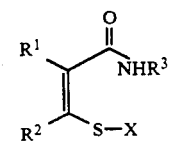

wherein
$R^1$ and $R^2$ taken together represent a polymethylene chain having 3 or 4 carbon atoms or a polymethylene chain having 3 or 4 carbon atoms substituted by at least one lower alkyl radical having from 1 to 4 carbon atoms;
$R^3$ is hydrogen, hydrocarbyl or hydrocarbyl substituted with at least one atom selected from the group consisting of oxygen, nitrogen, sulphur and halogen;
X represents cyano, a group $—SO_3M$ or a group $—S—R^4$;
M represents a cation having a valency and being in an amount to give a neutral compound; and
$R^4$ represents hydrocarbyl or hydrocarbyl substituted with at least one atom selected from the group consisting of oxygen, nitrogen, sulphur and halogen, 21. A method for inhibiting the growth of micro-organisms on, or in, a medium, which comprises treating the medium with a compound which is
2-methylaminocarbonyl-1-thiocyanatocyclopent-1-ene,
the sodium salt of 2-methylaminocarbonyl-1-thiosulphatocyclopent-1-ene,
the sodium salt of 2-butylaminocarbonyl-1-thiosulphatocyclopent-1-ene,
the sodium salt of 2-hexylaminocarbonyl-1-thiosulphatocyclopent-1-ene,
the sodium salt of 2-octylaminocarbonyl-1-thiosulphatocyclopent-1-ene, or
1-tertiarybutyldithio-2-methylaminocarbonylcyclopentene.

22. A method as claimed in claim 20 wherein the medium which is treated is a cooling water system, a paper mill liquor, a metal working fluid, a geological drilling lubricant, a polymer emulsion, a paint, a lacquer, a varnish, a hydrocarbon fluid, an adhesive, a cosmetic, a dyestuff or ink formulation, an agrochemical formulation, leather or wood.

23. A medium susceptible to microbial attack comprising a compound having the formula

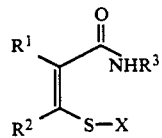 I wherein
R¹ and R² taken together represent a polymethylene chain having 3 or 4 carbon atoms or a polymethylene chain having 3 or 4 carbon atoms substituted by at least one lower alkyl radical having from 1 to 4 carbon atoms;

R³ represents hydrogen, hydrocarbyl or hydrocarbyl substituted with at least one atom selected from the group consisting of oxygen, nitrogen, sulphur and halogen, X represents cyano, —SO$_3$M or —S—R⁴;

M represents a cation having a valency and being in an amount to give a neutral compound; and R⁴ represents hydrocarbyl or hydrocarbyl substituted with at least one atom selected from the group consisting of oxygen, nitrogen, sulphur and nitrogen;

said compound of formula I being present in an amount effective to inhibit the growth of microorganisms on, or in, said medium.

* * * * *